US009259597B2

(12) United States Patent
Romano et al.

(10) Patent No.: US 9,259,597 B2
(45) Date of Patent: *Feb. 16, 2016

(54) METHOD OF TREATING AN OCULAR PATHOLOGY BY APPLYING ULTRASOUND TO THE TRABECULAR MESHWORK AND DEVICE THEREOF

(75) Inventors: Fabrizio Romano, Rillieux-la-Pape (FR); Philippe Chapuis, Pommiers (FR); Laurent Farcy, Liergues (FR); Thomas Charrel, Lyons (FR)

(73) Assignees: EYE TECH CARE, Rillieux-la-Pape (FR); INSTITUTE NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/202,084

(22) PCT Filed: Aug. 26, 2009

(86) PCT No.: PCT/EP2009/061014
§ 371 (c)(1),
(2), (4) Date: Aug. 17, 2011

(87) PCT Pub. No.: WO2010/094353
PCT Pub. Date: Aug. 26, 2010

(65) Prior Publication Data
US 2011/0301507 A1    Dec. 8, 2011

(30) Foreign Application Priority Data
Feb. 18, 2009   (WO) ................ PCT/EP2009/051892

(51) Int. Cl.
*A61H 1/00*     (2006.01)
*A61N 7/02*     (2006.01)
(Continued)

(52) U.S. Cl.
CPC .. *A61N 7/02* (2013.01); *A61N 7/00* (2013.01); *A61F 9/00745* (2013.01);
(Continued)

(58) Field of Classification Search
CPC ............................ A61N 7/00; A61H 23/0245
USPC ........................................................... 601/2
See application file for complete search history.

(56) References Cited

U.S. PATENT DOCUMENTS

| 4,484,569 A | 11/1984 | Driller et al. |
| 4,634,418 A | 1/1987 | Binder |

(Continued)

FOREIGN PATENT DOCUMENTS

| DE | 44 30 720 | 6/1995 |
| DE | 202 21 042 | 12/2004 |

(Continued)

OTHER PUBLICATIONS

Coleman et al; "Therapeutic Ultrasound in the Treatment of Glaucoma"; I. Experimental Model; Opthamology; 1985; vol. 92; pp. 339-346.
(Continued)

*Primary Examiner* — Tse Chen
*Assistant Examiner* — Hien Nguyen
(74) *Attorney, Agent, or Firm* — Miles & Stockbridge PC

(57) ABSTRACT

A phacoemulsificator for the removal of lens tissue, wherein the phacoemulsificator contains:
  a power source configured to provide pulsed electrical power, and
  a pump configured to provide vacuum, characterized in that the phacoemulsificator contains at least one eye ring connectable to the pump wherein the proximal end of said eye ring is suitable to be applied onto an ocular globe and means to generate ultrasound beam connectable to the power source wherein said means are fixed on the distal end of the eye ring.

11 Claims, 2 Drawing Sheets

(51) Int. Cl.
*A61N 7/00* (2006.01)
*A61F 9/007* (2006.01)

(52) U.S. Cl.
CPC ...... *A61F 9/00781* (2013.01); *A61N 2007/006* (2013.01); *A61N 2007/0056* (2013.01); *A61N 2007/0078* (2013.01)

(56) References Cited

U.S. PATENT DOCUMENTS

| | | | |
|---|---|---|---|
| 4,787,885 A | | 11/1988 | Binder |
| 4,936,825 A | | 6/1990 | Ungerleider |
| 4,946,436 A | | 8/1990 | Smith |
| 5,127,901 A | | 7/1992 | Odrich |
| 5,180,362 A | | 1/1993 | Worst |
| 5,230,334 A | | 7/1993 | Klopotek |
| 5,360,399 A | | 11/1994 | Stegmann |
| 5,433,701 A | | 7/1995 | Rubinstein |
| 5,533,998 A | | 7/1996 | Freese et al. |
| 5,591,127 A | * | 1/1997 | Barwick et al. ............ 604/66 |
| 5,779,723 A | | 7/1998 | Schwind |
| 5,860,994 A | * | 1/1999 | Yaacobi ............ 606/166 |
| 6,039,689 A | | 3/2000 | Lizzi |
| 6,267,752 B1 | * | 7/2001 | Svetliza ............ 604/294 |
| 2002/0009015 A1 | * | 1/2002 | Laugharn et al. ............ 366/108 |
| 2002/0016557 A1 | | 2/2002 | Duarte et al. |
| 2002/0055736 A1 | | 5/2002 | Horn et al. |
| 2002/0169130 A1 | * | 11/2002 | Tu et al. ............ 514/12 |
| 2004/0015140 A1 | | 1/2004 | Shields |
| 2007/0239011 A1 | | 10/2007 | Lau et al. |
| 2008/0275370 A1 | * | 11/2008 | McIntyre et al. ............ 601/2 |

FOREIGN PATENT DOCUMENTS

| | | |
|---|---|---|
| EP | 0 627 207 | 12/1994 |
| EP | 1 243 236 | 9/2002 |
| EP | 1 306 068 | 5/2003 |
| EP | 1 325 722 | 7/2003 |
| EP | 1 350 492 | 10/2003 |
| EP | 1 738 725 | 1/2007 |
| FR | 2 906 165 | 3/2008 |
| RU | 2 197 926 | 2/2003 |
| RU | 2 200 522 | 3/2003 |
| SU | 591186 | 7/1976 |
| WO | 96/14019 | 5/1996 |
| WO | 96/28213 | 9/1996 |
| WO | 97/07755 | 3/1997 |
| WO | 01/80708 | 11/2001 |
| WO | 02/38078 | 5/2002 |
| WO | 2006/018686 | 2/2006 |
| WO | 2006/065671 | 6/2006 |
| WO | 2006/136912 | 12/2006 |
| WO | 2007/081750 | 7/2007 |
| WO | 2008/024795 | 2/2008 |
| WO | 2008/115455 | 9/2008 |

OTHER PUBLICATIONS

Mueller; "Focusing Water Shock Waves for Lithotripsy by Various Ellipsoid Reflectors"; Biomed Tech (BERL).; Apr. 1989; vol. 34; No. 4; pp. 62-72.

Lizzi et al.; "Ultrasonic Therapy and Imaging in Ophthalmology"; 1985; pp. 1-17; XP-002079832.

Rouland et al.; "An Observational, Retrospective Two-Year Cost Study in Primary Open-Angle Glaucoma and Ocular Hypertension in Newly Diagnosed Patients"; J Fr. Ophtalmol.; 2001; vol. 24; No. 3; pp. 233-243; Masson, Paris.

Bron et al.; "Prevalence of Intraocular Hypertension and Glaucoma in a Nonselected French Population"; J Fr. Ophtalmol.; 2006; vol. 29; No. 6; pp. 635-641; Masson, Paris.

Chavrier et al.; "Modeling of High-Intensity Focused Ultrasound-Induced Lesions in the Presence of Cavitation Bubbles"; J. Acoust. Soc. Am; Jul. 2000; vol. 108; No. 1; pp. 432-440.

Lachkar et al.; "Depistage Du Glaucomechronique A Angle Ouvert"; 2001; 14 Pages.

Haute Autorite De Sante (HAS_; "Depistage Et Diagnostic Precoce Du Glaucome: Problematique Et Perspectives En France"; Recommandation En Sante Publique Rapport D'Orientation; Nov. 2006; 70 Pages.

Hamard et al.; "Traitement Des Glaucomes Refractaires"; Ophtalmologie; 1997; 8 Pages.

International Search Report Based on International Application No. PCT/EP2009/061014 Mailed Mar. 10, 2010.

* cited by examiner

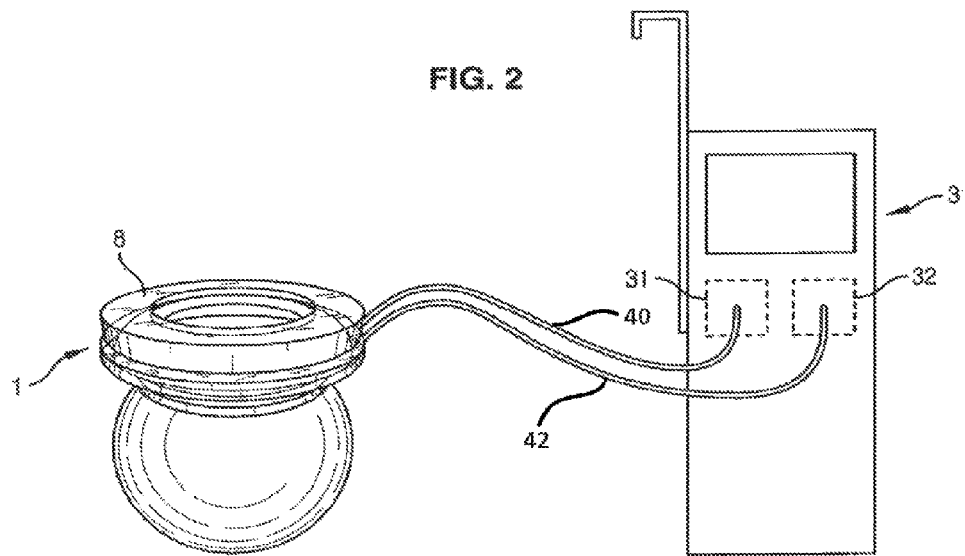
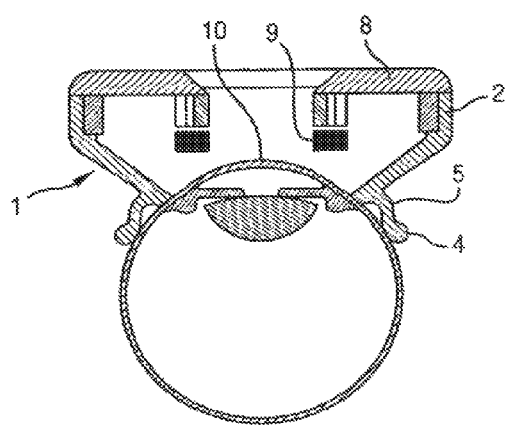

METHOD OF TREATING AN OCULAR PATHOLOGY BY APPLYING ULTRASOUND TO THE TRABECULAR MESHWORK AND DEVICE THEREOF

CROSS REFERENCE TO RELATED APPLICATIONS

This application is a §371 National Stage Application of PCT/EP2009/061014 filed Aug. 26, 2009, which claims priority to PCT/EP2009/051892 filed Feb. 18, 2009.

BACKGROUND OF THE INVENTION

1. Field of the Invention

The present invention is generally directed to a surgical treatment for ocular pathology, and relates more particularly to a device and method for generating ultrasound onto at least one annular segment of the trabecular meshwork of an eye affected by glaucoma 2. Description of Related Art In the field of ophthalmologic diseases, one of the main surgical act that is practiced is cataract surgery.

Cataracts cause the lens of an eye to become clouded, which interferes with proper transmission and focusing of light on the retina.

A common practice to alleviate this condition is by surgically removing the cataractic lens and replacing it with an artificial intraocular lens.

Phacoemulsification enables the removal of a cataractic lens through a small incision, for example between about 2.5 to about 4 mm.

In this procedure, a needle is inserted through the incision into the capsular bag of the crystalline lens and the needle is ultrasonically vibrated to mechanically emulsify the lens nucleus.

Once fragmented, or emulsified, the lens material is aspirated through a lumen through the phacoemulsification needle.

While emulsifying the lens and aspirating lens fragments, a simultaneous flow of irrigation fluid into the lens capsule is provided around the needle through an annulus established by a sleeve concentrically disposed over the needle.

This flow of liquid into the eye is necessary to prevent collapse of the anterior chamber of the eye during aspiration. In addition, the irrigation fluid cools the needle in order to prevent any thermal damage of the corneal or scleral tissue.

Phacoemulsification machines are very popular in the field of ocular medicine, and many surgeons have a phacoemulsificator for practicing cataract surgery.

It has to be noticed that the patients having a cataract often have a glaucoma. This is mainly due to the fact that both cataract and glaucoma affects most frequently aged patients.

It is well known that glaucoma is a significant public health problem, between 1 to 2% of population being suffering from this pathology, because glaucoma is a major cause of blindness.

The World health organisation considers glaucoma as the third cause of blindness in the world, responsible of 15% of declared blindness occurrences, with an incidence of 2.4 millions persons per year.

The evolution of glaucoma is slow. Glaucoma is an insidious health disease because at the first stage glaucoma is asymptomatic; the patient does not feel any pain or any visual problem. When the first visual troubles appear, lesions are commonly already large and despite irreversible.

The blindness that results from glaucoma involves both central and peripheral vision and has a major impact on an individual's ability to lead an independent life.

Glaucoma is an optic neuropathy, i.e. a disorder of the optic nerve, which usually occurs in the setting of an elevated intraocular pressure. The pressure within the eye increases and this is associated with changes in the appearance and function of the optic nerve. If the pressure remains high enough for a long period of time, total vision loss occurs. High pressure develops in an eye because of an internal fluid imbalance.

The eye is a hollow structure that contains a clear fluid called "aqueous humor." Aqueous humor is formed in the posterior chamber of the eye by the ciliary body. The fluid, which is made at a fairly constant rate, then passes around the lens, through the pupillary opening in the iris and into the anterior chamber of the eye. Once in the anterior chamber, the fluid drains out of the eye through two different routes. In the "uveoscleral" route, the fluid percolates between muscle fibers of the ciliary body. This route accounts for approximately ten percent of the aqueous outflow in humans. The primary pathway for aqueous outflow in humans is through the "canalicular" route that involves the trabecular meshwork and Schlemm's canal.

With the increased pressure in the eye, the aqueous fluid builds up because it cannot exit fast enough. As the fluid builds up, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to abnormally elevated IOP than other eyes.

One approach to treat glaucoma consist in trying to improve aqueous humor drainage.

The most practiced surgeries intended to improve the aqueous humor drainage are: canaloplasty, laser trabeculoplasty, laser peripheral iridotomy (in case of angle closure glaucoma), trabeculectomy, deep non perforating sclerectomy and glaucoma drainage implants.

Canaloplasty is an advanced, nonpenetrating procedure designed to enhance and restore the eye's natural drainage system to provide sustained reduction of IOP. Canaloplasty utilizes breakthrough micro catheter technology in a simple and minimally invasive procedure. To perform a canaloplasty, a doctor will create a tiny incision to gain access to a canal in the eye. A micro catheter will circumnavigate the canal around the iris, enlarging the main drainage channel and its smaller collector channels through the injection of a sterile, gel-like material. The catheter is then removed and a suture is placed within the canal and tightened. By opening the canal, the pressure inside the eye will be relieved.

Laser trabeculoplasty may be used to treat open angle glaucoma. A laser spot is aimed at the trabecular meshwork to stimulate opening of the mesh to allow more outflow of aqueous fluid. Usually, half of the angle is treated at a time.

There are two types of laser trabeculoplasty:

Argon laser trabeculoplasty (ALT) uses a laser to open up the drainage angle of the eye.

Selective laser trabeculoplasty (SLT) uses a lower-level laser to obtain the same result.

Laser peripheral iridotomy may be used in patients susceptible to or affected by angle closure glaucoma. During laser iridotomy, laser energy is used to make a small full-thickness opening in the iris. This opening equalizes the pressure between the front and back of the iris, causing the iris to move backward.

The most common conventional surgery performed for glaucoma is the trabeculectomy. Here, a partial thickness flap is made in the scleral wall of the eye, and a window opening made under the flap to remove a portion of the trabecular meshwork. The scleral flap is then sutured loosely back in place. This allows fluid to flow out of the eye through this opening, resulting in lowered intraocular pressure and the formation of a bleb or fluid bubble on the surface of the eye under the conjunctiva.

Trabeculectomy is associated with many problems. Fibroblasts that are present in the episclera proliferate and migrate and can scar down the scleral flap. Failure from scarring may occur, particularly in children and young adults. Of eyes that have an initially successful trabeculectomy, eighty percent will fail from scarring within three to five years after surgery. To minimize fibrosis, surgeons now are applying antifibrotic agents such as mitomycin C (MMC) and 5-fluorouracil (5-FU) to the scleral flap at the time of surgery. The use of these agents has increased the success rate of trabeculectomy but also has increased the prevalence of hypotony. Hypotony is a problem that develops when aqueous flows out of the eye too fast. The eye pressure drops too low (usually less than 6.0 mmHg); the structure of the eye collapses and vision decreases. Antimetabolites directly applied on the surgical site can be used in order to improve the surgical prognosis, especially in high risk of failure (black patients, juvenile glaucoma . . . ).

Trabeculectomy creates a pathway for aqueous fluid to escape to the surface of the eye. At the same time, it creates a pathway for bacteria that normally live on the surface of the eye and eyelids to get into the eye. If this happens, an internal eye infection can occur called endophthalmitis. Endophthalmitis often leads to permanent and profound visual loss. Endophthalmitis can occur anytime after trabeculectomy. Another factor that contributes to infection is the placement of a bleb. Eyes that have trabeculectomy performed inferiorly have about five times the risk of eye infection than eyes that have a superior bleb. Therefore, initial trabeculectomy is performed superiorly under the eyelid, in either the nasal or temporal quadrant.

In addition to scarring, hypotony and infection, there are other complications of trabeculectomy. The bleb can tear and lead to profound hypotony. The bleb can be irritating and can disrupt the normal tear film, leading to blurred vision. Patients with blebs generally cannot wear contact lenses. All of the complications from trabeculectomy stem from the fact that fluid is being diverted from inside the eye to the external surface of the eye.

More recently a new surgical technique has been described, called Non-perforating deep sclerectomy ab externo. This technique allows avoiding to open the anterior chamber of the eye and consequently reduces the risk of postoperative complications. The major limitation of this technique is that it is a very difficult surgical technique and only a few surgeons are able to perform it successfully.

When trabeculectomy or sclerectomy doesn't successfully lower the eye pressure, the next surgical step often is an aqueous shunt device. There are several different glaucoma drainage implants. These include the original Molteno implant, the Baerveldt tube shunt, or the valved implants, such as the Ahmed glaucoma valve implant or the ExPress Mini Shunt and the later generation pressure ridge Molteno implants. These are indicated for glaucoma patients not responding to maximal medical therapy, with previous failed guarded filtering surgery (trabeculectomy). The flow tube is inserted into the anterior chamber of the eye and the plate is implanted underneath the conjunctiva to allow flow of aqueous fluid out of the eye into a chamber called a bleb.

The prior art includes a number of such aqueous shunt devices, such as U.S. Pat. No. 4,936,825, U.S. Pat. No. 5,127,901, U.S. Pat. No. 5,180,362, U.S. Pat. No. 5,433,701, U.S. Pat. No. 4,634,418, U.S. Pat. No. 4,787,885, U.S. Pat. No. 4,946,436, U.S. 20040015140A1 and U.S. Pat. No. 5,360,399.

Many complications are associated with aqueous shunt devices. A thickened wall of scar tissue that develops around the plastic plate offers some resistance to outflow and in many eyes limits the reduction in eye pressure. In some eyes, hypotony develops because the flow through the tube is not restricted. The surgery involves operating in the posterior orbit and many patients develop an eye muscle imbalance and double vision post-operatively. Moreover, because they are open to the surface of the eye, a pathway is created for bacteria to get into the eye and endophthalmitis can potentially occur.

SUMMARY OF THE INVENTION

An aim of the present invention is to provide a device for improving aqueous humor drainage, said device being adaptable on a phacoemulsification machine. This procedure could be performed systematically before cataract surgery in patients with early stage Intraocular Pressure (IOP) rising, to reduce the risk for them to develop a glaucoma. In fact many patients with cataract, have also an abnormally elevated IOP, as in both cases aged patients have higher risk to develop both pathologies. For those patients where this elevation is still not severe, it could be useful to take advantage of the cataract procedure to perform a preventive treatment to avoid further elevation of the IOP leading to a glaucoma. In those patients, trabecular meshwork could be "cleaned" with an ultrasonic method, just before the cataract procedure so that all the debris removed from the trabecular meshwork will be washed out by the phacoemulsification hand-piece and the irrigation/aspiration circuit during cataract surgery.

The above-mentioned need is addressed by the embodiments described herein in the following description of the invention which allows treating the whole circumference of the eye in only one step, without the necessity to manipulate the device during the procedure.

In one embodiment, a phacoemulsificator for the removal of lens tissue is disclosed. The phacoemulsificator comprises:
a power source configured to provide pulsed electrical power, and
a pump configured to provide vacuum.

The phacoemulsificator is remarkable in that it comprises at least one eye ring connectable to the pump wherein the proximal end of said eye ring is suitable to be applied onto an ocular globe and means to generate ultrasound beam connectable to the power source wherein said means are fixed on the distal end of the eye ring.

BRIEF DESCRIPTION OF THE DRAWINGS

FIGS. 1-3 represent embodiments as described herein.

DETAILED DESCRIPTION OF A PREFERRED EMBODIMENT

Figure 1:
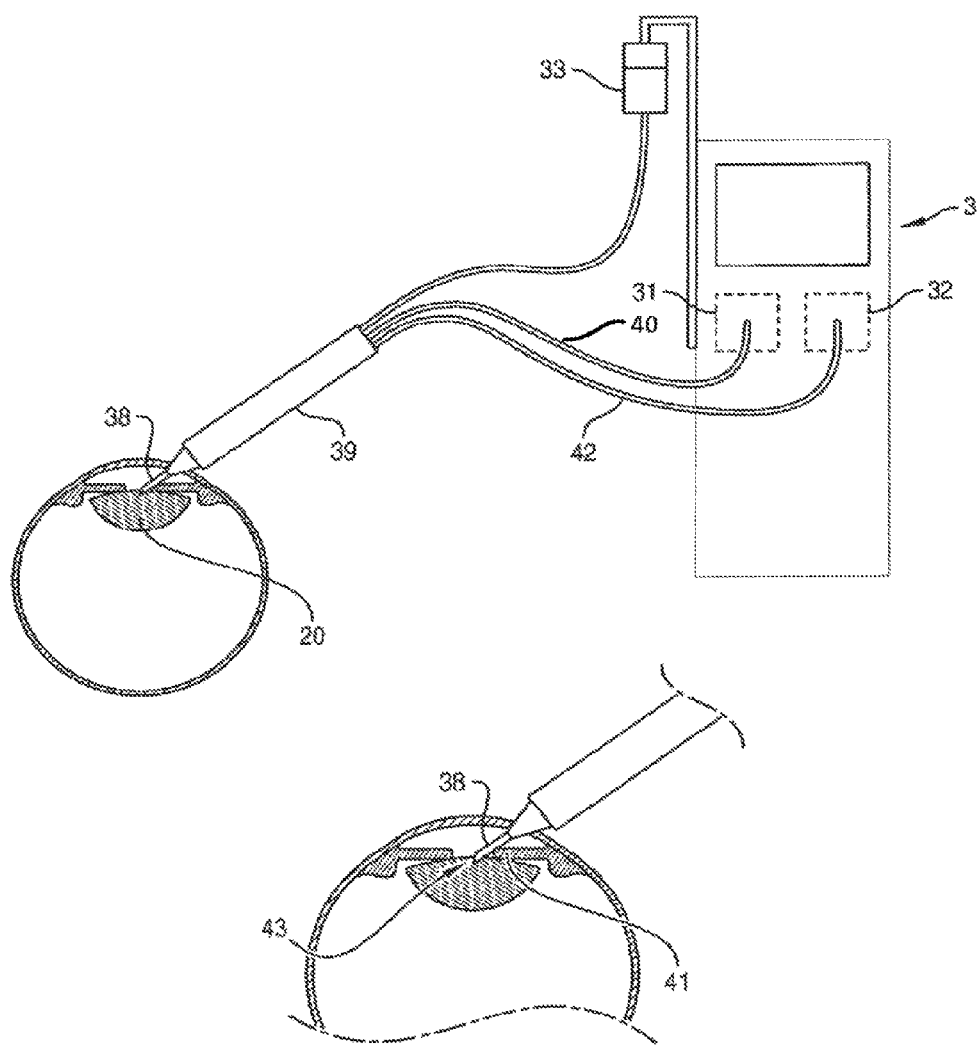

Preferably, the means fixed on the distal end of the eye ring composed of piezoelectric transducers are suitable to generate scattered ultrasound beam.

The eye ring may consist in a sawn-off cone element open at both ends wherein the small base is the proximal end and the large base is the distal end. The proximal end of the sawn-off cone element may comprise an external annular flange suitable to be applied onto the eye globe. The proximal edge of the sawn-off cone element may further comprise an annular groove communicating with at least one hose formed in the sawn-off cone element and connected to the pump. The sawn-off cone element may be in medical grade silicon or in medical grade polymer.

In one embodiment, the means to generate ultrasound energy comprise a unique transducer having an annular shape, fixed on the distal end of the sawn-off cone element in such a way that said transducer extend toward the revolution axis of said sawn-off cone element. The transducer may have a flat segment shape. The means to generate ultrasound energy may include a focusing acoustic lens extending under the flat transducer.

In another embodiment, the means to generate ultrasound beam fixed on the distal end of the eye ring comprise a plurality of transducers arranged according to a treatment pattern. In particular, the means to generate ultrasound beam comprise a housing, the transducers being placed peripherally over the housing according to the treatment pattern. More particularly said transducers are placed peripherally over the whole or a part of the housing, and more preferably the transducers are circumferentially placed over the whole or a part of the circumference of the housing.

The invention further concerns a method of treating an ocular pathology by generating ultrasound onto at least one eye's area. The method comprises at least the following steps of:
  connecting an eye ring to a pump configured to provide vacuum,
  connecting means to generate ultrasound beam to a power source configured to provide pulsed electrical power,
  positioning the eye ring and the means to generate ultrasound beam onto the eye for directing ultrasound onto at least one annular segment,
  generating ultrasound energy onto said segment to treat at least one annular segment in the eye.

Preferably, the ultrasound energy is generated onto at least one annular segment corresponding to at least one segment of the trabecular meshwork of the eye. In a variant of the invention, the method further comprises implementing a cataract surgery after having treated said annular segment.

The apparatus and the method according to the present invention allows:
  simplifying the operation procedure by providing a device which allows a treatment of the eye in one time; indeed, once the apparatus is placed and fixed onto the eye, the apparatus stay in position and the treatment of the whole circumference of the eye can be realized without the need for the operator to displace or maintain the apparatus,
  providing a reproducible procedure; indeed unlike the apparatus of the prior art, the device of the present invention do not need to be displaced many times to treat different punctual zones of the region to be treated,
  reducing the operative time which reduces the error risk factor and thus improve the quality of the treatment,
  providing a treatment which is less dependent from the operator, because very easy to be performed, very easy to be learned with an extremely short learning curve, and relatively automatic during the treatment time.

It will be understood in the case of the present invention that the treatment pattern corresponds to the form defined by the regions to be treated. In the case of the treatment of the trabecular meshwork, the treatment pattern may be annular or semi-annular. In other cases, the treatment pattern may be elliptical, or hexagonal or octagonal.

Embodiments of varying scope are described herein. In addition to the aspects described in this summary, further aspects will become apparent by reference to the drawings and with reference to the detailed description that follows.

FIG. 1 is a representation of a phacoemulsificator,

FIGS. 2 and 3 are a schematic perspective view of the device for treatment of an ocular pathology by applying ultrasound energy according to the invention.

We will disclose hereinafter a method and a device suitable for the treatment of glaucoma; nevertheless, it is obvious that the skilled person could adapt the method and the device for the treatment of any ophthalmologic pathology that necessitate surgery without departing of the scope of the invention.

As described in WO 2008/024795, ultrasound can be used for their vibrating properties on small particles for the treatment of glaucoma.

In patients with too high intra ocular pressure, and with open angle glaucoma, the problem is that the trabecular meshwork is no longer efficient enough to allow aqueous humor to be drained properly to Schlemm's canal. Trabeculum permeability is lower than normally, due to the fact that trabecular spaces are blocked with small particles as pigments, cell debris, fibrin, etc. . . . .

The device according to the invention can easily produce a vibration obtained with the propagation of an ultrasonic beam, transmitted to the trabecular meshwork, which unlike the apparatus described in WO 2008/024795 can concern the whole circumference of the trabeculum at the same time, more rapidly and in only one step, as will be apparent from the detailed description that follows.

Advantageously, the present invention for the treatment of glaucoma is adaptable to existing devices for the treatment of cataract by phacoemulsification. This allows limiting the number of apparatus necessary to implement a cataract treatment and a glaucoma treatment during the same surgical procedure.

A phacoemulsificator is an apparatus for the removal of lens tissue.

As show on FIG. 1, a phacoemulsificator generally includes a control unit 3 comprising:
  a power source 31 configured to generate pulsed electrical power
  a pump 32 configured to provide vacuum, and
  a liquid source 33 configured to provide an irrigation fluid.

A first needle 38 is ultrasonically vibrated by a handpiece 39. The handpiece 39 is interconnected:
  to the power source 31 of the control unit 3 through a power line 40, and
  to the pump 32 of the control unit 3 through an aspiration line 42.

The first needle is designated to be introduced through the cornea and the anterior capsule in the crystalline lens nucleus 20.

The first needle 38 fragments or emulsifies the cataractic lens which is then aspirated along with irrigation fluid through a lumen 41 in the needle 38 as indicated by the arrow 43.

The needle 38 includes an aspiration port defined by the lumen 41. The aspiration port allows aspirating the fluid from the capsular bag 20.

As mentioned above, the device according to the present invention is adaptable on the control unit 3 of a phacoemulsificator with the need of an upgrade of the software.

More particularly, the power source 31, and the pump 32 of the control unit can be used to connect different elements that will be described in more details below. The connection of these elements with the control unit 3 of a phacoemulsificator allows preventing/treating glaucoma by generating ultrasound onto the trabecular meshwork of the eye in order to improve drainage efficiency of trabeculum.

Referring to FIG. 2, the device according to the invention comprises an eye ring 1 wherein the proximal end of said eye ring is suitable to be applied onto the globe of the eye to be treated and (see FIG. 3) means 2 to generate ultrasound energy, said means being fixed on the distal end of the eye ring.

Said means are connected to the control unit 3 of the phacoemulsificator. More particularly, said means 2 are connected to the power source 31 configured to provide pulsed electrical power.

Preferably, the means 2 generates ultrasounds that are not High Intensity Focussed Ultrasound.

Indeed, the aim of generating ultrasound onto the trabecular meshwork is to get the trabecular meshwork to vibrate in order to improve the drainage efficiency.

The control unit 3 may comprise means specifying the parameters such as the frequency, the power and the duration of the ultrasound generation, etc. . . . The power source 31 comprises at least a sine-wave signal generator at a determined frequency comprised between 1 kHz and 25 MHz, an amplifier and a Power meter.

Referring to FIGS. 2 and 3, the eye ring 1 consists in a sawn-off cone element opened at both ends wherein the small base is the proximal end and the large base is the distal end.

Referring to FIG. 3, the proximal end of the sawn-off cone element 1 comprises an external annular flange 4 suitable to be applied onto the external surface of the eyeglobe, at approximately 2 mm of the limbus, the limbus being the junction between the cornea and sclera of the eyeglobe. The proximal face of the annular flange 4 presents a concave profile, the radius of curvature of the concave profile being substantially equal to the radius of curvature of the eyeglobe.

Moreover, the proximal edge of the sawn-off cone element 1 comprises an annular groove 5 connected to the pump 32 of the control unit by at least one hose 7 passing through the sawn-off cone element 1 and emerging into the annular groove. The pump 32 is used as a suction device which is advantageously controlled by the control unit 3.

When the sawn-off cone element 1 is applied onto the eye and the pump 32 is operated, the depression into the annular groove 5 provide a deformation of the conjunctiva of the eye, said deformation forming an o-ring in the annular groove 5. The sawn-off cone element 1 is then closely interlinked in such a manner that said sawn-off cone element 1 will follow the micro movements of the eye during the whole treatment time, and maintaining the quality of the centred position of the device on the visual axis.

The sawn-off cone element 1 is advantageously obtained in medical grade silicon or other medical grade polymer which are materials compatible with the conjunctiva contact.

It is obvious that the sawn-off cone element 1 can be obtained in any suitable material for medical purposes well known by the skilled person, and which has been verified as biocompatible, such as biocompatible PVC, without departing with the scope of the invention.

Referring to FIGS. 2 and 3, means 2 to generate ultrasound beam comprise a standing crown 8 holding a single transducer 9 having an annular shape.

In one embodiment, the transducer 9 has a flat section shape. Said single transducer 9 having a flat section can be associated to a focusing acoustic lens extending under said transducer 9—i.e. held by the standing crown 8 and extending between the proximal edge of the standing crown 8 and the proximal edge of the sawn-off cone element 1. In this case, the focusing acoustic lens presents a cylindrical shape and a concave edge wherein the concavity is tuned towards the eyeglobe, and more particularly towards the trabecular meshwork, to focalize the ultrasound beam onto the area of interest, i.e. the trabecular meshwork of the eye.

In another embodiment, the transducer 9 has a concave section shape, wherein the concavity is designated to be tuned toward the eyeglobe, and more particularly toward the trabecular meshwork. In this case, this is the concave section shape of the transducer 9 which allows the focalization of the ultrasound beam onto the trabecular meshwork of the eye.

The external radius of said standing crown 8 is sensibly equal to the internal diameter of the distal end of the sawn-off cone element 1.

In this way, the standing crown 8 extends toward the revolution axis of said sawn-off cone element 1. Said transducer 9 is held in the proximal edge of the standing crown 8.

The transducer 9 is activated by the control unit 3 to produce a vibration obtained with the propagation of an ultrasonic beam, transmitted to the trabecular meshwork over the whole or a part of its circumference.

In this manner, by positioning correctly the sawn-off cone element 1 onto the eye to be treated, as described hereinafter, the whole or a part of the trabecular meshwork is treated without the need to manipulate the device during the treatment.

Advantageously, the means 2 to generate ultrasound beam may comprise a standing crown and a plurality of elementary transducers 9 disposed with respect to one another so as to define an annular shape.

For instance, the standing crown 8 of transducers 9 may comprise six transducers 9. Each transducer 9 is a cylindrical segment able to treat 60° of the circumference of the trabecular meshwork.

It will be noted that the standing crown 8 can comprise two or more transducers 9 distributed among the circumference in any manner without departing with the scope of the invention.

To apply correctly the sawn-off cone element 1 onto the eye, the surgeon must manipulate the sawn-off cone element 1 as far as the iris ring and the periphery of the cornea are centred in the distal opening of the sawn-off cone element 1. If the white ring corresponding to the visible part of the sclera trough the opening of the proximal end of the ring, has a constant thickness, the centring is correct. When the sawn-off cone element 1 is centred on the pupil, the revolution axis of said sawn-off cone element 1 and the optical axis of the eye are merging. Consequently, the planes in which extend the distal edge and the proximal edge of the sawn-off cone element 1 are perfectly parallel to the planes of the eye such as iris plane, pupil plane or plane of the trabecular meshwork, and the transducer 9 is at the plumb of the trabecular meshwork 10. This allows a better positioning of the device according to the invention, and improves the reproducibility of the treatment.

Moreover, the device can comprise two aiming wires 14 extending crosswise and diametrally from the internal edge of the standing crown 8 or another centring system like a circular pad supposed to be centred on the pupil. This allows facilitating the centring of the sawn-off cone element with regard to the eye. To centre the sawn-off cone element 1, it is necessary to centre the intersection of the aiming wires 14 with the centre of the pupil.

It will be understood that the device according to the invention can comprise other centring system known from the man skilled in the art for facilitating the centring of the sawn of cone.

When the sawn-off cone element 1 is correctly centred onto the eye, the pump 32 is activated to interlink said sawn-off cone element 1 with the eye. The depression into the annular groove 5 provides a deformation of the conjunctiva of the eye, said deformation forming an o-ring in the annular groove 5. This insures a proper maintain in position of the device during all the treatment.

The sawn-off cone element 1 is then filled with a physiological saline degassed solution, the o-ring formed by the deformation of the conjunctiva of the eye in the annular groove ensuring the sealing. The physiological saline solution provides a cooling of the eye and the device during the generation of ultrasound beam and an ultrasound coupling media that permits the propagation of ultrasound from transducer 9 to area of interest, i.e. the trabecular meshwork 10. Note that the physiological saline solution moisturizes the cornea of the eye during the treatment.

It is obvious that the physiological saline degassed solution could be substituted by any ultrasound coupling agent such as aqueous media or lipophilic media without departing of the scope of the invention.

Then, the frequency and/or the power and/or the duration of each pulse are selected or already predetermined and the transducer 9 (or the plurality of transducers) is (are) activated by the control unit 3 to produce a vibration of the trabecular meshwork over the whole or a part of the circumference.

Note that the treatment according to the invention is advantageously a short treatment which can be performed before the phacoemulsification procedure with the same machine.

The device according to the invention can easily produce a vibration obtained with the propagation of an ultrasonic beam, transmitted to the trabecular meshwork, which unlike the apparatus described in WO 2008/024795 can concern the whole circumference of the trabeculum at the same time, more rapidly and in only one step. Moreover, with the device according to the invention, thanks to the ring which allows centering and fixation on the eye globe, this technique can be substantially improved compared to the device described in WO 2008/024795.

The fact that the device according to the present invention, used as a treatment of open angle glaucoma with the vibration technique applied on the trabecular meshwork, can be combined with a phacoemulsification machine has many advantages. In particular, this allows implementing both treatments (cataract and glaucoma) during a single procedure, which improves the treatment by the vibration technique.

In fact, when the particles like cell debris, fibrin, pigment or other, responsible for the loss of drainage efficiency of trabeculum, are delivered from their adherence to the trabecular meshwork, and are circulating in the aqueous humor it is obvious that they will rapidly be cached again by trabeculum, reducing consequently the efficiency of the treatment by the vibration technique.

If implementing the glaucoma treatment before the cataract surgery, then the particles delivered from their adherence thanks to the vibration technique according to the invention will be aspirated during the cataract surgery.

Thus the idea is to combine the glaucoma treatment with a phacoemulsification machine, and preferably during a cataract surgery, because during this surgery the anterior chamber and the liquid it contains, are completely washed with a balanced salt solution circulating in the irrigation/aspiration circuit, so that if the vibration technique is performed before the cataract surgery, all the debris delivered from their adherence on the trabecular meshwork, will be washed out of the anterior chamber, increasing the efficiency of the treatment.

It is well known that cataract surgery is more frequent in older population. It is well known too that glaucoma is more frequent in the same population.

For this reason, combined surgeries, including cataract and trabeculectomy are more and more frequent.

This written description uses examples to disclose the invention, including the best mode, and also to enable any person skilled in the art to make and use the invention. The scope of the subject matter described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of treating glaucoma by generating ultrasound onto at least one eye's area wherein the method comprises at least the following:
   connecting an eye ring to a pump to provide vacuum,
   connecting a generator for generating ultrasound beam to a power source to provide pulsed electrical power, and to generate a sine-wave signal in a range of 1 kHz to 25 MHz,
   positioning the eye ring and the generator onto the eye for directing ultrasound onto at least one annular segment,
   generating ultrasound energy onto said segment to treat at least one annular segment corresponding to at least one segment of a trabecular meshwork of the eye,
   wherein the procedure to treat only glaucoma takes place in a single step: and wherein the entire circumference of the eye is treated in one step.

2. The method according to claim 1 wherein the ultrasound energy is generated onto at least one annular segment corresponding to at least one segment of the trabecular meshwork of the eye.

3. A method according to claim 1 further comprising implementing a cataract surgery after having treated said annular segment.

4. A method according to claim 1 wherein the entire circumference of the eye is treated in one step.

5. A method according to claim 1 wherein the ultrasound energy comprises scattered ultrasound beam.

6. A method according to claim 1 wherein the eye ring comprises a sawn-off cone element open at both ends wherein a small base is the proximal end and the large base is the distal end, and
   wherein the proximal end of the sawn-off cone element comprises an external annular flange,
   wherein the external annular flange is applied onto the eye globe.

7. A method according to claim 6 wherein the annular flange is applied at approximately 2 mm of the limbus.

8. A method according to claim 1,
   wherein the eye ring comprises a sawn-off cone element open at both ends wherein a small base is the proximal end and the large base is the distal end,
   wherein the proximal edge of the sawn-off cone element comprises an annular groove communicating with at least one hose formed in the sawn-off cone element and connected to the pump and
   wherein the sawn-off cone element is applied onto the eye and the pump is operated, the depression into the annular groove provide a deformation of the conjunctiva of the eye, said deformation forming an o-ring in the annular groove.

9. A method according to claim 8, wherein the sawn-off cone element is then closely interlinked in such a manner that said sawn-off cone element follows the micro movements of the eye during the whole treatment time.

10. A method according to claim 8, wherein the sawn-off cone is filled with an ultrasound coupling agent, the o-ring ensuring the sealing, the ultrasound coupling agent providing a cooling of the eye during the generation of ultrasound beam and an ultrasound coupling media that permits the propagation of ultrasound to the trabecular meshwork.

11. A method according to claim 8, wherein the frequency and/or the power and/or the duration of each pulse are selected or predetermined to produce a vibration of the trabecular meshwork over the whole or a part of the circumference.

* * * * *